United States Patent
Kleemann et al.

(10) Patent No.: US 9,726,664 B2
(45) Date of Patent: Aug. 8, 2017

(54) ANIMAL MODEL FOR DIABETIC COMPLICATIONS

(75) Inventors: Robert Kleemann, Delft (NL); Reinout Stoop, Delft (NL); Johan Hendrikus Verheijen, Delft (NL); Peter Ydo Wielinga, Delft (NL); Teake Kooistra, Delft (NL)

(73) Assignee: NEDERLANDSE ORGANISATIE VOOR TOEGEPAST—NATUURWETENSCHAPPELIJK ONDERZOEK TNO, Delft (NL)

( * ) Notice: Subject to any disclaimer, the term of this patent is extended or adjusted under 35 U.S.C. 154(b) by 426 days.

(21) Appl. No.: 13/885,199

(22) PCT Filed: Nov. 14, 2011

(86) PCT No.: PCT/NL2011/050776
§ 371 (c)(1),
(2), (4) Date: Jun. 25, 2013

(87) PCT Pub. No.: WO2012/067503
PCT Pub. Date: May 24, 2012

(65) Prior Publication Data
US 2013/0324423 A1  Dec. 5, 2013

(30) Foreign Application Priority Data
Nov. 15, 2010  (WO) ................ PCT/NL2010/050757

(51) Int. Cl.
*G01N 33/50*   (2006.01)
*G01N 33/68*   (2006.01)

(52) U.S. Cl.
CPC ..... *G01N 33/5088* (2013.01); *G01N 33/6893* (2013.01); *G01N 2800/042* (2013.01); *G01N 2800/347* (2013.01)

(58) Field of Classification Search
CPC ............................................. G01N 2800/042
See application file for complete search history.

(56) References Cited

PUBLICATIONS

Wouters et al. (Hepatology. 2008; 48: 474-486).*
Wouters et al (Hepatology 2008; 48: 474-486).*
Wu et al. (Atherosclerosis. 2007; 191: 241-249).*
PCT, International Search Report, PCT/NL2011/050776 (mailed Jan. 26, 2012), 3 pages.
Wouters et al. Dietary Cholesterol, Rather than Liver Steatosis, Leads to Hepatic Inflammation in Hyperlipidemic Mouse Models of Nonalcoholic Steatohepatitis. Hepatology, vol. 48, No. 2 (2008), pp. 474-486. XP-002666551.
Heinonen et al. Increased Atherosclerotic Lesion Calcification in a Novel Model Combining Insulin Resistance, Hyperglycemia, and Hypercholesterolemia. Circulation Research, vol. 101, No. 10 (2007), pp. 1058-1067. Online Data Supplement—Materials and Methods (6 pages). XP-002634001.
Taneja et al. Reversability of renal injury with cholesterol lowering in hyperlipidemic diabetic mice. Journal of Lipid Research, vol. 51 (2010), pp. 1464-1470. XP009147473.
Lam et al. Cholesterol-lowering therapy may retard the progression of diabetic nephropathy. Diabetologia, vol. 38 (1995), pp. 604-609. XP009143834.
Hammad et al. Nephropathy in a Hypercholesterolemic Mouse Model with Streptozotocin-Induced Diabetes. Kidney and Blood Pressure Research, vol. 26 (2003), pp. 351-361. XP009147474.
Subramanian et al. Dietary cholesterol exacerbates hepatic steatosis and inflammation in obese LDL receptor-deficient mice. Journal of Lipid Research, vol. 52 (2011), pp. 1626-1635. XP009155154.

* cited by examiner

Primary Examiner — Scott Long
(74) Attorney, Agent, or Firm — Thompson Hine LLP

(57) ABSTRACT

The invention relates to the surprising find that low density lipoprotein receptor-deficient mice (LDLr−/−) mice when fed with high energy diets produce controllable and consistent diabetic complications, especially renal damage, similar to the human pathophysiology and biological response. The invention thus comprises a method for discovering a preventive or therapeutic regimen for the prevention or treatment of diabetic micro- or macrovascular complications, comprising the steps of: a. feeding LDLr−/− mice, which have not been treated with streptozotocin, with a high energy diet; b. before, during and/or after this diet treating the mice with the preventive or therapeutic regimen; c. checking whether any change in the micro- or macrovascular system of the animal occurs. Specifically in such a method renal damage is assessed. Also use of said mice fed with a high energy diet for studying the diabetic micro- and macrovascular complications is part of the invention.

6 Claims, 5 Drawing Sheets

ANIMAL MODEL FOR DIABETIC COMPLICATIONS

FIELD OF THE INVENTION

Figure 1:
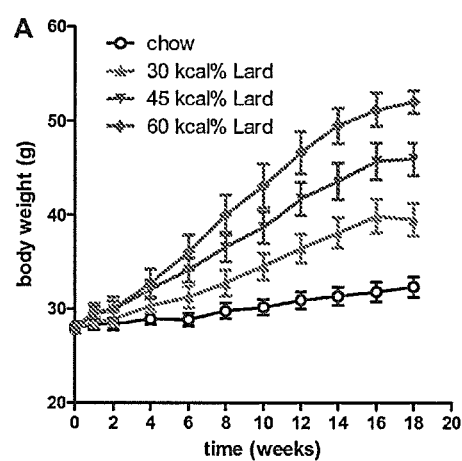

The invention relates to the field of diabetes, more particularly complications caused by diabetes or diabetes-like phenomena, like insulin resistance, metabolic syndrome and such, especially diabetic complications such as micro- and macrovascular complications, retinopathy, hepatopathy and diabetic nephropathy. More particularly, the invention relates to an animal model for such complications, in particular diabetic nephropathy and methods for finding therapies for the prevention of diabetes induced tissue damage and particularly renal damage.

BACKGROUND

Nephropathy is a complication which is often seen in diabetes, as well with diabetes type 1, diabetes type 2, pre-diabetes, gestational as drug-induced diabetes. There are wide differences in estimates of how many people with diabetes will progress to having diabetic kidney disease—from 6 to 27 percent of people with Type 1 diabetes, to 25 to 50 percent of Type 2. Diabetic disease is characterized by high levels of blood glucose which is associated with tissue damage. Small vascular and capillary structures are very sensitive to diabetes-induced injury and organs such as the kidney are frequently affected. By endothelial and microvascular damage the kidneys start to become 'leaky' which is first diagnosed on basis of increased protein levels in the urine (microalbuminuria). If no intervention follows, this develops in an even higher level of proteins in the urine (macroalbuminuria), glucosuria and finally in end-stage renal disease (ESRD) which necessitates dialysis or kidney transplantation.

Diabetic nephropathy is the major cause of ESRD worldwide, and its incidence has increased by more than 50% in the past ten years (USRDS 2008 Annual Data Report: Atlas of Chronic Kidney Disease and End-Stage Renal Disease in the Unites States, NIH).

Similar micro- and macrovascular complications that play a role in renal damage also can result in other forms of complications, such as retinopathy. It is likely that micro- and macrovascular dysfunction also play a role in the development other diabetes-associated pathologies such as neuropathy, hepatopathy, hepatosteatosis, adipose inflammation (e.g. in visceral adiposity) and pancreas dysfunction.

Lack of reliable, translational animal models that sufficiently mimic the multifactorial human pathofysiology have prevented optimal development of insight in the disease mechanism and candidate therapy/drug development. Therefore, much effort has been devoted to develop animal models for this specific complication in diabetes (see: Brosius, F. C. et al., 2009, J. Am. Soc. Nephrol. 20:2503-2512). Some mouse models have been described in this overview, but it is considered that there is still need for more, and/or more comprehensive animal models. Some of the drawbacks of the present models are: i) that diabetic complications develop heterogeneously with great variations between animals (despite comparable genetic make-up and age) and ii) that the severity of diabetic complications, especially microalbuminuria, does not progress over time as it is the case in humans.

SUMMARY OF THE INVENTION

The inventors now have surprisingly found that low density lipoprotein receptor-deficient mice ($LDLr^{-/-}$) mice when fed with high energy diets produce controllable, progressively developing and consistent diabetic complications, especially renal damage, similar to the human pathophysiology and biological response.

The invention thus comprises a method for discovering a preventive or therapeutic regimen for the prevention or treatment of diabetic micro- or macrovascular complications, comprising the steps of:
  a. feeding $LDLr^{-/-}$ mice, which have not been treated with streptozotocin, with a high energy diet;
  b. before, during and/or after this diet treating the mice with the preventive or therapeutic regimen;
  c. checking whether any change in the micro- or macrovascular system of the animal occurs.

More specifically, the invention relates to a method for discovering a preventive or therapeutic regimen for the prevention or treatment of diabetic nephropathy (and microalbuminuria), comprising the steps of:
  a. feeding $LDLr^{-/-}$ mice, which have not been treated with streptozotocin, with a high energy diet;
  b. before, during and/or after this diet treating the mice with the preventive or therapeutic regimen;
  c. checking whether any change in the protein content of the urine of said mice occurs and or whether any histological or immunohistological change in the kidneys of said mice occurs.

Preferably in a method according to the invention, the preventive or therapeutic regimen is administration of a medicament or combination of medicaments, wherein the medicaments in said combination may be administered concomitantly or sequentially. Alternatively the preventive or therapeutic regimen is a life style intervention or a combination of a life style intervention and one or more medicaments.

Also part of the invention is the use of LDLr-/- mice for study regarding the aetiology, progression, prevention, and treatment of diabetic macro- and microvascular complications, in which mice said complications have not been effected by streptozotocin induced diabetes. More specifically, these diabetic complications are selected from the group of diabetic neuropathy, diabetic hepatosteatitis, impaired wound healing, glucosuria and diabetic retinopathy, or combinations thereof.

LEGENDS TO THE FIGURES

FIG. 1: The increase in body weight is correlated to the concentration of fat in the diet.

Figure 2:
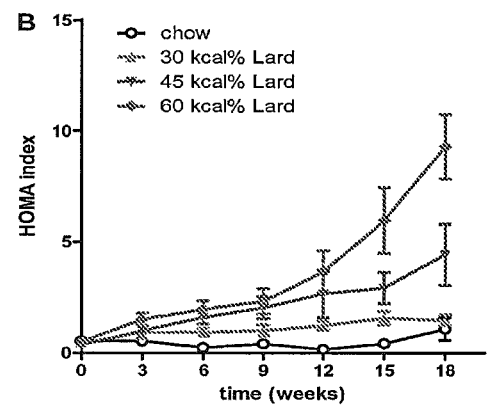

FIG. 2: HOMA values are dose-dependently increased by intake of fat through the diet.

Figure 3:
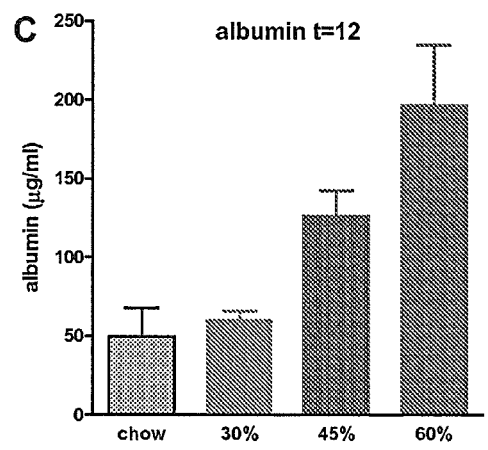

FIG. 3: Dose dependent increase in urinary protein concentration (Y-axis) in relation to fat content in the diet. The protein content of the urine is generally expressed as the albumin to creatinine ratio, where the level of albumin is typically expressed in µg/ml while the level of creatinine is typically expressed in mg/ml.

Figure 4:
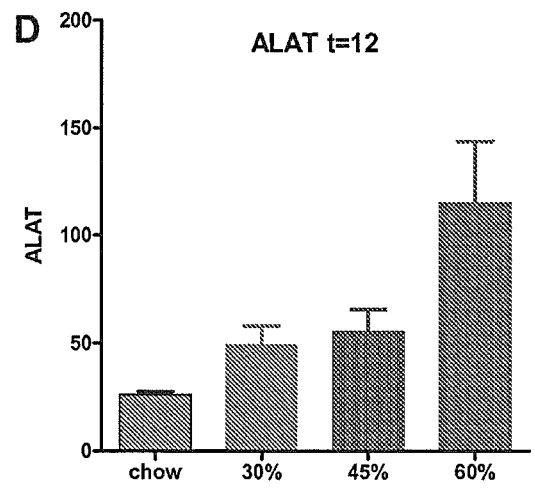

FIG. 4: ALAT-values caused by high-energy diets.

Figure 5:
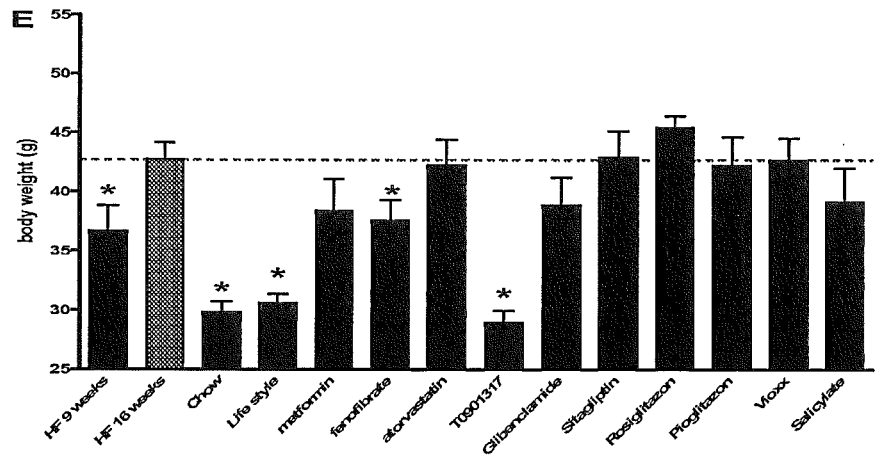

FIG. 5: Body weight in $LDLr^{-/-}$ mice fed with high energy diet after pharmaceutical and life style interventions.

Figure 6:
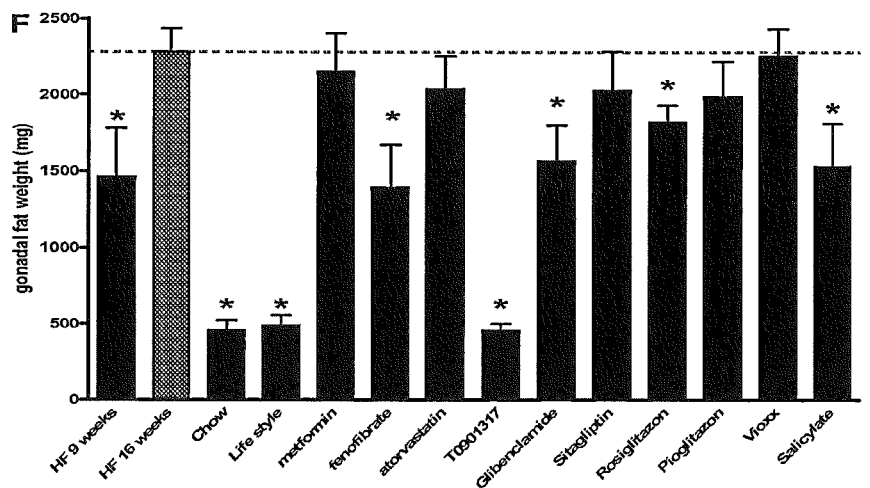

FIG. 6: Gonadal fat mass in $LDLr^{-/-}$ mice fed with high energy diet after pharmaceutical and life style interventions.

Figure 7:
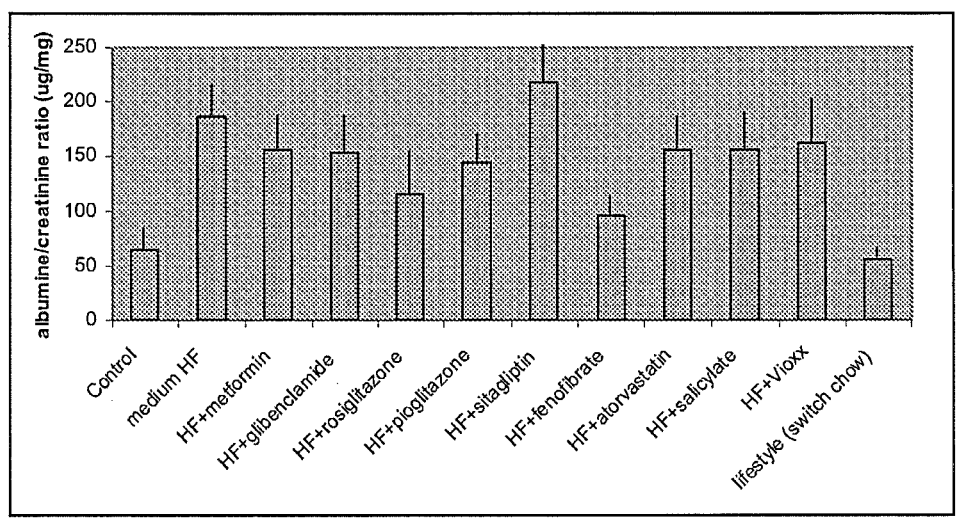

FIG. 7: Concentration of protein in urine in $LDLr^{-/-}$ mice fed with high energy diet after pharmaceutical and life style interventions.

Figure 8:
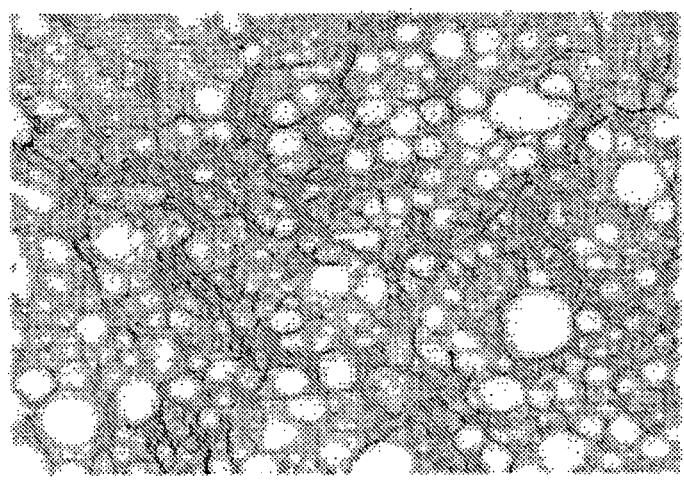

FIG. 8: Histology of the liver. Clearly shown are the lipid droplets and collagen depositions.

DETAILED DESCRIPTION

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs.

LDLr$^{-/-}$ mice as first described by Ishibashi, S. et al. in 1994 (J. Clin. Invest. 93:1885-1893, 1994) are mice that do not or no longer express an active LDL receptor protein, preferably in which the gene coding for said LDL-receptor has been knocked out. They are commonly used for research purposes in the field of lipid metabolism and atherosclerosis.

Protein content of the urine is expressed as the albumin/creatinine ratio as is discussed in detail in the Examples.

Nephropathy or renal damage is the condition in which the function of the kidneys is deteriorated, which condition includes morphological manifestations of renal tissue damage, microalbuminuria, macroalbuminuria, fatty degeneration, tissue necrosis, glucosuria, kidney fibrosis and end-stage renal disease (ESRD).

High energy diets are diets in which the lipid content is increased, especially in the form of fats or oils. Preferably animal fats, such as lard, beef tallow, butter, and ghee are used. These diets are typical diabetogenic diets and they also induce obesity. Some plant-derived fats are also diabetogenic, for instance palm oil based diets. All the above diabetogenic diets contain a high content of saturated fatty acids and monosaturated fatty acids and relatively little polyunsaturated fatty acids (PUFAs). When diabetogenic diets are fed to susceptible animals, such as LDLr$^{-/-}$ mice or apoE3 Leiden mice, these animals will develop human-like features of the metabolic syndrome and/or diabetes.

LDLr$^{-/-}$ mice have been used already for some years in the research for atherosclerosis using atherogenic diets. Atherogenic diets differ from diabetogenic diets in several ways: they typically contain less fat (in w/w % as well as in En %) and they typically are supplemented with cholesterol at a concentration of 0.1% w/w and 1% w/w). Some investigators also add chocolate to the atherogenic diets to stimulate cholesterol uptake and to increase plasma cholesterol. A typical atherogenic diet contains for instance 15% w/w cocoa and 1% w/w palm oil and 1% cholesterol as fat source (as reported in Kleemann et al. Genome Biology, 2007). An overview of the most frequently used atherogenic diets (clearly differing from diabetogenic diets) is also provided in Zadelaar et al., ATVB, 2007). The LDLR-/- mice, being deficient for the LDL-receptor protein have been found to have severe elevated plasma LDL cholesterol levels when fed a atherogenic diet. and increased LDL cholesterol is associated with aortic atherosclerotic lesion development (Ishibashi, S. et al., 1994, J. Clin. Invest. 93:1885-1893).

In these mice it has also been proven feasible to introduce a diabetes like syndrome by treating them with a chemical substance that targets the pancreas, streptozocin (STZ), a method that has been applied in several animal models to introduce a diabetes type 1 like state by damaging pancreatic cells by STZ (McEvoy, R. C. et al., 1984, J. Clin. Invest. 74:715-722). Further, it is known that STZ-induction of type 1 diabetes in LDLR$^{-/-}$ mice is associated with (spontaneous nephropathy (Hammad, S. M., 2003, Kidney Blood Press. Res. 26:351-361; Taneja, D., et al. 2010, J. Lipid Res. 51:1464-1470) http://www.ncbi.nlm.nih.gov/pubmed/8182121.

The present inventors now surprisingly found that feeding LDLr$^{-/-}$ mice with a high energy diet did not only increase plasma LDL cholesterol, triglyceride levels, plasma glucose levels, plasma sVCAM-1, plasma E-selectin, plasma SAA, plasma insulin levels and plasma C-peptide levels (the latter clearly demonstrating intact pancreatic beta cells) thereby enabling their uses as animal model for insulin resistance/metabolic syndrome and atherosclerosisbut they also found that these mice developed diabetic complications, in particular a nephropathy, as revealed by microalbuminuria, which behaved dose-dependently in respect to the amount of fat ingested with the food. This nephropathy thus developed under conditions leading to diet-inducible type 2 diabetes and without an STZ induction, and thus not only resembles the human aetiology of the disease, but also led to similar, micro- as well as macrovascular complications and pathophysiology. Notably, LDLR-/- mice fed diabetogenic diets exhibit elevated plasma insulin levels and elevated C-peptide levels at the same time point when microalbuminuria is observed indicating that pancreatic beta cells are still intact and functioning (C-peptide is co-secreted with insulin from pancreatic beta-cells). This clearly demonstrates that the microalbuminuria of the present invention is unrelated to the STZ-induced microalbuminuria which has been reported by others (see references above).

The high energy diet caused already notable symptoms of diabetic disease including microalbuminuria within 10-15 weeks after the start of high fat diet feeding, which means that the animal model of the current invention can be obtained relatively rapidly, and is thus suitable for pharmacological studies.

Importantly, diabetic complications in this model i) are diet-inducible in a dose-dependent way; ii) renal disease also progresses over time (increasing extent of microalbuminuria); and iii) the complications, especially the renal damage, are similar to the human pathophysiology and biological responses. Lastly, the extent of renal disease is reversible and can be modulated by both dietary interventions (including lifestyle) as well as with drugs.

The animal is very well suited to study the aetiology of diabetic nephropathy and the influences of external factors, drugs, lifestyle changes (such as change in diet and/or body exercise), aging, hormonal status, stress, inflammatory tone on the development of the nephropathy. Possible therapeutic interventions, not only for the prevention of diabetic nephropathy, but also for the treatment of this complication can easily be accommodated by using this animal model. The severity of the disease state can easily be monitored by determining the amount of protein in the urine (albuminuria).

Accordingly, the invention relates to a new method for discovering preventive and therapeutic strategies for the prevention or treatment of diabetic nephropathy comprising the steps of a) feeding LDLr$^{-/-}$ mice with a high energy diet; b) before, during and/or after this diet treating the mice with the preventive or therapeutic regimen and c) checking whether any change in the protein content of the urine of said mice occurs. It should be understood that the 'preventive or therapeutic regimen' mentioned above can be a medicament or a combination of medicaments, including neutraceuticals and biologicals (administered concomitantly or sequentially), but also a change in lifestyle, or a combination of both. A change in lifestyle may include a change to another diet, or any further interference, such as a change in housing conditions (such as climatic conditions, day-night rhythm, social environment (solitary or group housing condition)), a change in feeding pattern, alternating feeding, change in stress, change in hormone treatment or a change in the level of physical exercise of the test animals, with respect to the animals of the control treatment.

The new model also allows to study the effects of preventive and therapeutic regimens on systemic and local inflammation.

Since the organs that are susceptible to diabetic complications including the kidney, the liver, the eye, the gut and the larger vessels are surrounded by adipose tissue and since adipose tissue may contribute to the development of diabetic complications in these tissues, the application of this newly developed model also comprises testing of preventive and therapeutic regimens directed at improving the function of liver (diabetic non-alcoholic steatosis, NASH and liver fibrosis), the function of the eyes (diabetic retinopathy), neuropathy induced impaired wound healing, the integrity and inflammatory state of the gut and the quantity and/or inflammatory status of adipose tissue itself. It has been shown in the experimental part of the present invention that liver abnormalities show in the mice model of the invention.

The invention will be illustrated in the following Example(s), which is for illustrative purpose and not deemed to be limiting the invention as claimed.

EXAMPLES

Experimental Set-Up

Groups of male LDLr−/− male mice (>12 weeks old) were fed a high fat diet for 20 weeks and monitored over time. Groups were treated with increasing concentrations of dietary fat as listed below (energy percentage from lard; En %) and a control group received chow.
1. chow control
2. 30 En % Lard diet
3. 45 En % Lard diet
4. 60 En % Lard diet Body weight and food intake were measured over time. Tail blood samples (4 h fasting blood) and spot urine were taken at regular time points (time points are indicated in graphs below; last plasma sample was taken in week 18) and analyzed for glucose, insulin, HOMA (Homeostatic Model Assessment), plasma lipids, systemic- and vascular inflammation as well as ALAT (alanine transaminase). At the end of the experiment, organs were collected, weighed and stored for future analysis.

Results

The above experimental set-up allowed definition of the most optimal concentration of lard in the diet to establish the hallmarks of human prediabetes, insulin resistance and overt diabetes.

A dose dependent increase in body weight was observed with increasing amount of dietary fat (FIG. 1). This increase in body weight was reflected by dose dependent increase in visceral- and subcutaneous adipose tissue. Both adipose depots have causatively been associated with the development cardiovascular and metabolic disease. By contrast, gonadal adipose tissue was comparably increased in the fat-treated groups. After 9 weeks of high fat treatment, the parameters indicative for prediabetes were manifest.

For example, glucose and insulin were markedly elevated by the two highest lard concentration and consequently also the HOMA value indicating a state of insulin resistance (FIG. 2). Plasma glucose levels in week 15 were 11.8 mM, 13.9 mM, 15.7 mM and 16.5 for group 1, 2, 3 and 4, respectively. Plasma C-peptide levels (C-peptide is co-secreted with insulin but has a greater plasma half-life) in week 12 were 2.0, 3.0, 3.1 and 3.7 ng/mL for group 1, 2, 3 and 4, respectively. Plasma cholesterol and plasma triglycerides were markedly elevated by all diets. More specifically, plasma cholesterol levels in week 18 were 8, 19, 24, 26 mM and plasma triglyceride levels in week 18 were 1, 3, 4, 5 mM for group 1, 2, 3, and 4, respectively. The increase in total plasma cholesterol was mainly confined to cholesterol in LDL particles (as revealed by lipoprotein analysis, not shown). Systemic inflammation (quantified by serum amyloid A in plasma) was 2.5, 7.1, 8.3, 22.8 µg/mL for group 1, 2, 3, and 4, respectively, and significantly increased with all three lard diets. Also vascular inflammation markers (VCAM and E-selectin) were significantly elevated indicating macro- and microvascular dysfunction, respectively (e.g. E-selectin in week 12: 79, 89, 86 and 90 ng/mL for group 1, 2, 3, and 4, respectively).

In line with microvascular damage, a dose dependent increase in microalbuminurea was observed (FIG. 3) which is a hallmark of nephropathy. Interestingly, the model exhibited a diet-inducible, homogenously developing microalbuminuria that developed gradually over time and in a dose-dependent fashion depending on the amount of fat in the diet. Finally, ALAT, a measure of liver function, was only slightly increased by 30% and 45% En lard, but was markedly increased by 60% En lard (FIG. 4).

Example 2

Based on the findings of the above experiment, an intervention study was designed. The middle dose (45 En % lard diet) was defined to be the optimal diet to use for interventions with drugs since ALAT was not increased Thereby putative adverse liver effects of drugs can still be detected. Several anti-diabetic interventions (drugs and life-style) were tested according to the experimental set-up described above.

LDLr−/− mice (12 weeks old) were fed 45 En % Lard diet for 9 weeks to establish a prediabetic state (as described above and including visceral adiposity, hypertriglyceridemia, elevated glucose and insulin, chronic inflammation). After these 9 weeks, the interventions were started and continued until week 16. Drugs were mixed into lard diet and administered orally via the feed. One group of mice was sacrifice at the start of the intervention at week 9 for reference. Another control group was fed chow throughout the 16 weeks (serving as internal reference). The groups were as follows:

1. Chow 15 weeks: healthy control ⎫
2. Lard 15 weeks: diseased control ⎬ controls
3. Lard 9 weeks: start intervention control ⎭
4. Metformin (250 mg/kg)
5. Sulphonylurea (Glibenclamide 10 mg/kg)
6. Rosiglitazone (10 mg/kg)
7. Pioglitazone (10 mg/kg)
8. DDP-IV inhibitor (Sitagliptin 20 mg/kg)
9. Fenofibrate (50 mg/kg)
10. Atovastatin (10 mg/kg)
11. LXR agonist (T0901317, 10 mg/kg)
12. Vioxx (34 mg/kg)
13. Salicylate (40 mg/kg)
14. Life style intervention (after 9 weeks Lard switch to chow)

Body weight and food intake were measured regularly and blood samples were taken at t=0, t=6, t=9, t=12, t=14 and t=15 weeks. Spot urine was collected at t=0, t=8 and t=15 weeks. At the end of the study, the mice were sacrificed and the various organs were isolated and weighed and stored at −80 C and/or in formalin. Livers were processed for microarray analysis. More specifically, the same lobe of each liver was used for RNA extraction to prepare mRNA of microarray quality according to an established protocol (Kleemann et al., Genome Biology, 2007).

Results of the intervention study: Mice that were fed lard for 16 weeks became obese while mice which were kept on chow did not develop symptoms of prediabetes confirming that the disease phenotype is induced by the diet. The first data demonstrate that the different interventions have differential effects on global health parameters (body weight, tissue weights, fat distribution over the various depots etc) and on microalbuminuria which appears to be reversible and which can be modulated with drugs. For instance, body weight (FIG. 5) was reduced by fenofibrate and LXR agonist, whereas body weight was slightly increased by rosiglitazone. Total adipose tissue was unaffected by rosiglitazone, while the distribution of the fat across the various depots was markedly affected with this drug (subcutaneous fat was increased while gonadal fat mass (FIG. 6) was reduced). Gonadal fat was also lowered by fenofibrate, sulphonylurea, LXR agonist and salicylate.

Interestingly, differential effects of the drugs on microalbuminuia were observed. Microalbuminuria is a hallmark of diabetic nephropathy and was determined by measuring the concentration of albumine and creatinine in spot urine collected at various time points during the experiment. Subsequently the albumine/creatinine ratio was calculated, viz. the amount of albumine expressed in μg per mg creatinine (FIG. 7). The drugs metformin, fenofibrate, atorvastatin, glibenclamide, rosiglitazone, pioglitazone and salicylate significantly improved the albumine/creatinine ratio compared to high fat treated control animals that were not treated with drugs. Since drugs were mixed into the high energy diet, the data indicate that these drugs interfere with diet-evoked diabetic nephropathy in a setting of type 2 diabetes. Notably, lifestyle intervention (switch to chow feeding) also reduced microalbuminuria to a level that was comparable to healthy control animals (FIG. 7) demonstrating that the disease phenotype is fully reversible.

Example 3

Male LDLr−/− mice (>12 weeks old) were fed a high fat diet (45% En % Lard diet) for 10 weeks, and for an additional 6 weeks high fat diet enriched with 1% (w/w) cholesterol.

Animals were sacrificed and livers were removed. Liver was weighed, fixed in formaldehyde and paraffin embedded. Tissue sections were stained for collagen using picrosirius red staining (0.1% Sirius Red in saturated aqueous picric acid solution) and analyzed microscopically.

It was observed (FIG. 8) that the histology very much resembled the histology seen in human steatosis/NASH (non-alcoholic liver steato hepatitis), as shown by Cohen, J. C. et al, Science 3332, 1519-1532, 24 Jun. 2011. Clear deposition of lipid droplets in the cytoplasm of hepatocytes, and significant collagen deposition (fibrosis) could be observed (FIG. 8). This means that the specific diet treated mice of the invention can also be used to assess the liver for steatosis like phenomena.

The invention claimed is:

1. A method for discovering a preventive or therapeutic regimen for the prevention or treatment of diabetic micro- or macrovascular complications, comprising the steps of:
   a) feeding LDLr$^{-/-}$ mice, which have not been treated with streptozotocin, with a high energy diet without supplemented cholesterol;
   b) before, during and/or after this diet treating the mice with the preventive or therapeutic regimen;
   c) checking whether any change in the micro- or macrovascular system of the animal occurs.

2. The method of claim 1, wherein the preventive or therapeutic regimen is administration of a medicament or combination of medicaments, wherein the medicaments in said combination may be administered concomitantly or sequentially.

3. The method of claim 1, wherein the preventive or therapeutic regimen is a life style intervention or a combination of a life style intervention and one or more medicaments.

4. The method of claim 1, wherein said micro- or macrovascular complication is selected from the group of nephropathy, retinopathy, neuropathy, hepatopathy, hepatosteatosis, adipose inflammation, pancreas dysfunction, impaired wound healing and glucosuria.

5. The method of claim 1, wherein the preventive or therapeutic regimen is selected from
   a medicament or a combination of medicaments,
   a change in lifestyle comprising
      a) a change of diet,
      b) a change of housing conditions,
      c) a change in feeding pattern,
      d) alternating feeding,
      e) a change in stress,
      f) a change in hormone treatment, and/or
      g) a change in the level of physical exercise,
   or a combination of both.

6. The method of claim 1 wherein the high energy diet without supplemented cholesterol comprises animal fats selected from lard, beef tallow, butter, and ghee.

* * * * *

UNITED STATES PATENT AND TRADEMARK OFFICE
CERTIFICATE OF CORRECTION

PATENT NO. : 9,726,664 B2  
APPLICATION NO. : 13/885199  
DATED : August 8, 2017  
INVENTOR(S) : Robert Kleemann et al.

Page 1 of 1

It is certified that error appears in the above-identified patent and that said Letters Patent is hereby corrected as shown below:

On the Title Page

Item (73) Assignee:  
Line 5, delete "Delft (NL)" and insert -- 'S-GRAVENHAGE (NL) --.

Signed and Sealed this  
Third Day of September, 2019

Andrei Iancu  
*Director of the United States Patent and Trademark Office*